(12) United States Patent
Mizutani et al.

(10) Patent No.: US 9,732,659 B2
(45) Date of Patent: Aug. 15, 2017

(54) SOX CONCENTRATION DETECTION DEVICE OF INTERNAL COMBUSTION ENGINE

(71) Applicant: TOYOTA JIDOSHA KABUSHIKI KAISHA, Toyota-shi, Aichi (JP)

(72) Inventors: Keigo Mizutani, Okazaki (JP); Shinya Teranishi, Aichi-ken (JP); Keiichiro Aoki, Shizuoka-ken (JP); Kazuhiro Wakao, Susono (JP); Toyoharu Kaneko, Susono (JP); Tatsuhiro Hashida, Shizuoka-ken (JP)

(73) Assignee: TOYOTA JIDOSHA KABUSHIKI KAISHA, Toyota-shi, Aichi (JP)

( * ) Notice: Subject to any disclaimer, the term of this patent is extended or adjusted under 35 U.S.C. 154(b) by 0 days.

(21) Appl. No.: 14/903,826

(22) PCT Filed: Jun. 13, 2014

(86) PCT No.: PCT/JP2014/003173
§ 371 (c)(1),
(2) Date: Jan. 8, 2016

(87) PCT Pub. No.: WO2015/004846
PCT Pub. Date: Jan. 15, 2015

(65) Prior Publication Data
US 2016/0146085 A1    May 26, 2016

(30) Foreign Application Priority Data

Jul. 12, 2013  (JP) .................................. 2013-146272
Jul. 12, 2013  (JP) .................................. 2013-146279

(51) Int. Cl.
*F01N 3/00*   (2006.01)
*F01N 11/00*  (2006.01)
(Continued)

(52) U.S. Cl.
CPC ............ *F01N 11/007* (2013.01); *F01N 11/00* (2013.01); *G01N 27/4065* (2013.01); *G01N 27/4074* (2013.01)

(58) Field of Classification Search
USPC .......................... 60/274, 276, 277, 297, 301
See application file for complete search history.

(56) References Cited

U.S. PATENT DOCUMENTS 5,667,652 A   9/1997   Liu et al.
6,051,123 A   4/2000   Joshi et al.
(Continued)

FOREIGN PATENT DOCUMENTS

JP  62-150153 A    7/1987
JP  H02-122255 A   5/1990
(Continued)

*Primary Examiner* — Binh Q Tran
(74) *Attorney, Agent, or Firm* — Andrews Kurth Kenyon LLP

(57) ABSTRACT

The object of the invention is to detect a concentration of a SOx included in an exhaust gas of an internal combustion engine easily and accurately by a limiting current type sensor. The invention relates to a SOx concentration detection device of the engine having a limiting current type sensor. The device of the invention comprises a detecting part for detecting the concentration of the SOx included in the exhaust gas by using an output current of the sensor while lowering a voltage applied to the sensor from a predetermined voltage.

17 Claims, 10 Drawing Sheets

(51) Int. Cl.
*G01N 27/406* (2006.01)
*G01N 27/407* (2006.01)

(56) References Cited

U.S. PATENT DOCUMENTS

| | | | |
|---|---|---|---|
| 8,555,699 B2* | 10/2013 | Otsuki | G01N 25/4873 60/277 |
| 8,695,399 B2* | 4/2014 | Nishioka | G01N 33/0042 73/23.31 |
| 2002/0173919 A1 | 11/2002 | Moteki et al. | |
| 2009/0077948 A1* | 3/2009 | Mondori | F01N 3/0842 60/285 |
| 2009/0320451 A1* | 12/2009 | Otsuki | B01D 53/9495 60/277 |
| 2014/0007560 A1* | 1/2014 | Fischer | F02D 41/144 60/276 |

FOREIGN PATENT DOCUMENTS

| | | |
|---|---|---|
| JP | 3-100454 A | 4/1991 |
| JP | H07-27738 A | 1/1995 |
| JP | 10-73561 A | 3/1998 |
| JP | H11-230931 A | 8/1999 |
| JP | 2002-349250 A | 12/2002 |
| JP | 2003293744 A | 10/2003 |
| JP | 2008-255952 A | 10/2008 |
| JP | 2009-244279 A | 10/2009 |

\* cited by examiner

Vs: APPLIED VOLTAGE
Is: OUTPUT CURRET
Csox: SOx CONCENTRATION

SOX CONCENTRATION DETECTION DEVICE OF INTERNAL COMBUSTION ENGINE

CROSS-REFERENCE TO RELATED APPLICATIONS

This is a national phase application based on the PCT International Patent Application No. PCT/JP2014/003173 filed Jun. 13, 2014, claiming priority to Japanese Patent Application Nos. 2013-146272 and 2013-146279 filed Jul. 12, 2013, the entire contents of all of which are incorporated herein by reference.

FIELD OF THE INVENTION

The invention relates to a SOx concentration detection device of an internal combustion engine.

BACKGROUND ART

A sensor for measuring a relative amount of an oxygen-included gas included in a gas mixture is described in Unexamined JP Patent Publication No. 2-122255. This sensor has two pump cells. These pump cells are positioned in series. In this sensor, a part of the oxygen-included gas (in particular, $O_2$) included in the gas mixture is removed by applying a lower voltage to the upstream-side pump cell and the relative amount of the remaining oxygen-included gas (in particular, $H_2O$ and $CO_2$) included in the gas mixture is measured by applying a high voltage to the downstream-side pump cell.

SUMMARY OF INVENTION

A limiting current type sensor is known. In this sensor, generally, a certain constant voltage is applied for the detection of a concentration of an oxygen included in an exhaust gas discharged from an internal combustion engine. However, according to this technique for applying the voltage, a concentration of a SOx included in the exhaust gas cannot be detected easily and accurately.

In this regard, from the study of the inventors of this application, it has been realized that when improving the technique for applying the voltage to the limiting current type sensor, the concentration of the SOx included in the exhaust gas can be detected accurately by the limiting current type sensor.

On the basis of this knowledge of the inventors of this application, the object of the invention is to accurately detect the concentration of the SOx included in the exhaust gas by the limiting current type sensor.

One invention of this application relates to a SOx concentration detection device of an internal combustion engine having a limiting current type sensor. The device of this invention comprises a detecting part for detecting a concentration of a SOx included in an exhaust gas discharged from the engine (hereinafter, this concentration of the SOx will be referred to as "SOx concentration") by using an output current of the sensor (hereinafter, this output current will be simply referred to as "output current") while lowering a voltage applied to the sensor (hereinafter, this voltage will be simply referred to as "applied voltage") from a predetermined voltage.

According to this, the SOx concentration can be detected. In particular, even in case that the influence of the SOx occupying the output current when the applied voltage is maintained at a constant voltage or the influence of the SOx occupying the output current when the applied voltage is raised is smaller than that of the other component occupying the output current, if the influence of the SOx occupying the output current when the applied voltage is lowered from the predetermined voltage is larger than that of the other component occupying the output current, the SOx concentration can be detected accurately.

Furthermore, it is preferred that the detecting part uses, as the output current for the detection of the SOx concentration, a peak value of the output current while lowering the applied voltage from the predetermined voltage. The peak value is a smallest output current (or a largest output current) of the output current during the lowering of the applied voltage. Therefore, the peak value is an output current accurately corresponding to the SOx concentration. Thus, the SOx concentration can be detected accurately by using the peak value as the output current for the detection of the SOx concentration.

Further, the detecting part may detect a concentration of an oxygen included in the exhaust gas by using the output current when a voltage lower than the predetermined voltage is applied to the sensor after lowering the applied voltage from the predetermined voltage. According to this, the concentration of the oxygen included in the exhaust gas and the SOx concentration can be detected by the single sensor.

Further, the detecting part may use, as the output current for the detection of the SOx concentration, the output current while lowering the applied voltage from the predetermined voltage after raising the applied voltage from a voltage lower than the predetermined voltage to the predetermined voltage. In this case, the voltage applied to the sensor prior to the start of the lowering of the applied voltage is lower than the predetermined voltage. Thus, comparing with the case that the voltage applied to the sensor prior to the start of the lowering of the applied voltage is equal to the predetermined voltage, an electric power consumed for the detection of the SOx concentration can be decreased.

The detecting part may detect a concentration of an oxygen included in the exhaust gas by using the output current when applying the voltage lower than the predetermined voltage before raising the applied voltage to the predetermined voltage. According to this, the concentration of the oxygen included in the exhaust gas and the SOx concentration can be detected by the single sensor.

Furthermore, it is preferred that the predetermined voltage is higher than or equal to 0.8V. According to this, the output current accurately corresponding to the SOx concentration can be obtained and as a result, the SOx concentration can be detected accurately.

Further, it is preferred that the applied voltage when the lowering of the applied voltage from the predetermined voltage is ended is a voltage lower than or equal to 0.7V. According to this, the output current accurately corresponding to the SOx concentration can be obtained and as a result, the SOx concentration can be detected accurately.

Furthermore, the detecting part may lower the applied voltage from the predetermined voltage at a speed smaller than or equal to a speed of a change of a voltage having 100 Hz. According to this, it is ensured that the output current accurately corresponding to the SOx concentration can be obtained and as a result, the SOx concentration can be detected accurately.

Further, the detecting part may raise the applied voltage from the voltage lower than the predetermined voltage and then, lower the applied voltage from the predetermined voltage at a speed smaller than or equal to a speed of a change of a voltage having 100 Hz. According to this, it is ensured that the output current accurately corresponding to the SOx concentration can be obtained and as a result, the SOx concentration can be detected accurately.

Furthermore, the engine is, for example, a gasoline engine. The gasoline engine is operated at a stoichiometric air-fuel ratio in a substantial part of an engine operation area. Therefore, a concentration of an oxygen included in an exhaust gas is low. Thus, the SOx concentration can be detected easily.

Further, the SOx concentration detection device may further comprise a controlling part for performing a sulfur poisoning regeneration control for regenerating the sulfur poisoning of the sensor in case that an absolute value of the output current while lowering the applied voltage from the predetermined voltage is larger than or equal to a first predetermined value. According to this, as far as the lowering of the accuracy of the detection by the sensor due to the sulfur poisoning may not occur, the SOx concentration is detected. Thus, the SOx concentration can be detected more accurately.

Furthermore, the SOx concentration detection device may further comprise a controlling part for alerting a malfunction of a property of a fuel supplied to a combustion chamber of the engine in case that an absolute value of the output current while lowering the applied voltage from the predetermined voltage is larger than a second predetermined value. According to this, in case that the malfunction of the property of the fuel may occur, a user of the SOx concentration detection device can realize that the malfunction of the property of the fuel may occur.

Another invention of this application relates to a method for detecting a concentration of a SOx included in an exhaust gas discharged from an internal combustion engine having a limiting current type sensor. This method comprises a voltage lowering step for lowering a voltage applied to the sensor from a predetermined voltage, an output current acquiring step for acquiring an output current of the sensor during the voltage lowering step and a SOx concentration detecting step for detecting the concentration of the SOx included in the exhaust gas by using the output current acquired by the output current acquiring step.

According to this, the SOx concentration can be detected. In particular, even in case that the influence of the SOx occupying the output current when the applied voltage is maintained at a constant voltage or the influence of the SOx occupying the output current when the applied voltage is raised is smaller than that of the other component occupying the output current, if the influence of the SOx occupying the output current when the applied voltage is lowered from the predetermined voltage is larger than that of the other component occupying the output current, the SOx concentration can be detected accurately.

Further, the method may further comprise a post-lowering voltage applying step for applying a voltage lower than the predetermined voltage to the sensor after the voltage lowering step and an oxygen concentration detecting step for detecting a concentration of an oxygen included in the exhaust gas by using the output current of the sensor during the post-lowing voltage applying step. According to this, the concentration of the oxygen included in the exhaust gas and the SOx concentration can be detected by the single sensor.

Furthermore, the method may further comprise a pre-lowering voltage applying step for applying a voltage lower than the predetermined voltage to the sensor before the voltage lowering step, a voltage raising step for raising the voltage applied to the sensor to the predetermined voltage after the pre-lowering voltage applying step and before the voltage lowering step and an oxygen concentration detecting step for detecting a concentration of an oxygen included in the exhaust gas by using the output current of the sensor during the pre-lowering voltage applying step. According to this, the concentration of the oxygen included in the exhaust gas and the SOx concentration can be detected by the single sensor.

Further another invention of this application relates to a limiting current type sensor. The limiting current type sensor of this invention is used for detecting a concentration of a SOx included in an exhaust gas discharged from an internal combustion engine by using an output current of the sensor while a voltage applied to the sensor is lowered from a predetermined voltage.

According to this, the limiting current type sensor for detecting the SOx concentration can be provided. In particular, even in case that the influence of the SOx occupying the output current when the applied voltage is maintained at a constant voltage or the influence of the SOx occupying the output current when the applied voltage is raised is smaller than that of the other component occupying the output current, if the influence of the SOx occupying the output current when the applied voltage is lowered from the predetermined voltage is larger than that of the other component occupying the output current, the limiting current type sensor for accurately detecting the SOx concentration can be provided.

Further, the sensor may be used for detecting a concentration of an oxygen included in the exhaust gas by using the output current of the sensor when a voltage lower than the predetermined voltage is applied to the sensor after the voltage applied to the sensor is lowered from the predetermined voltage. According to this, the concentration of the oxygen included in the exhaust gas and the SOx concentration can be detected by the single sensor.

Furthermore, the sensor may be used for detecting a concentration of an oxygen included in the exhaust gas by using the output current of the sensor when a voltage lower than the predetermined voltage is applied to the sensor before the predetermined voltage is applied to the sensor. According to this, the concentration of the oxygen included in the exhaust gas and the SOx concentration can be detected by the single sensor.

MODE FOR CARRYING OUT THE INVENTION

With reference to the drawings, embodiments of a limiting current type sensor of the invention and a SOx concentration detection device of an internal combustion engine comprising the limiting current type sensor will be described.

<Configuration of 2 Cell Type Limiting Current Type Sensor>

Figure 1:
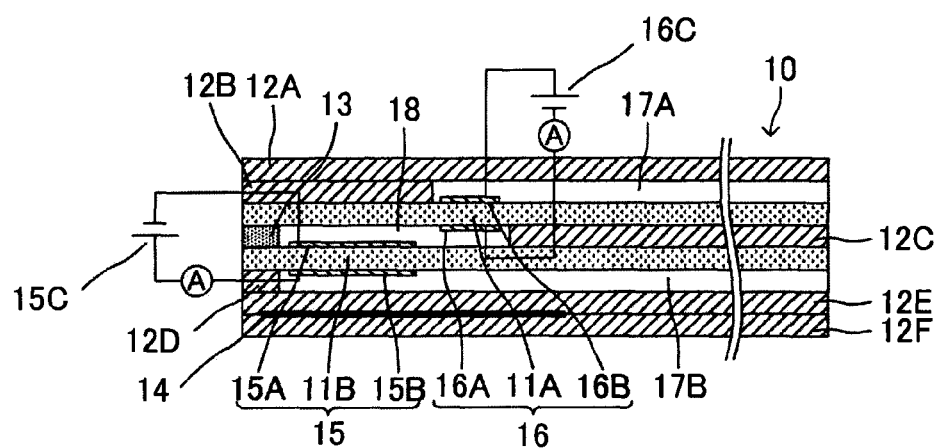
FIG. 1 shows an embodiment of a limiting current type sensor of the invention (2 cell type limiting current type sensor).

A limiting current type sensor according to the first embodiment of the invention is shown in FIG. 1. The sensor shown in FIG. 1 is a 2 cell type limiting current type sensor. In FIG. 1, 10 denotes the limiting current type sensor, 11A denotes a first solid electrolyte layer, 11B denotes a second solid electrolyte layer, 12A denotes a first alumina layer, 12B denotes a second alumina layer, 12C denotes a third alumina layer, 12D denotes a fourth alumina layer, 12E denotes a fifth alumina layer, 12F denotes a sixth alumina layer, 13 denotes a diffusion-limited layer, 14 denotes a heater, 15 denotes a pump cell, 15A denotes a first pump electrode, 15B denotes a second pump electrode, 15C denotes a pump cell voltage source, 16 denotes a sensor cell, 16A denotes a first sensor electrode, 16B denotes a second sensor electrode, 16C denotes a sensor cell voltage source, 17A denotes a first atmospheric air introduction passage, 17B denotes a second atmospheric air introduction passage and 18 denotes an interior space.

The solid electrolyte layers 11A and 11B are layers formed of zirconia or the like and have oxygen ion conductive properties. The alumina layers 12A to 12F are layers formed of alumina. The diffusion-limited layer 13 is a porous layer which can pass the exhaust gas therethrough. In the sensor 10, the layers are laminated such that the sixth alumina layer 12F, the fifth alumina layer 12E, the fourth alumina layer 12D, the second solid electrolyte layer 11B, the diffusion-limited layer 13 and the third alumina layer 12C, the first solid electrolyte layer 11A, the second alumina layer 12B and the first alumina layer 12A are positioned in order from the lower side of FIG. 1. The heater 14 is positioned between the fifth and sixth alumina layers 12E and 12F.

The first atmospheric air introduction passage 17A is a space formed by the first and second alumina layers 12A and 12B and the first solid electrolyte layer 11A and a part thereof opens to the atmosphere. The second atmospheric air introduction passage 17B is a space formed by the second solid electrolyte layer 11B and the fourth and fifth alumina layers 12D and 12E and a part thereof opens to the atmosphere. The interior space 18 is a space formed by the first and second solid electrolyte layers 11A and 11B, the diffusion-limited layer 13 and the third alumina layer 12C and a part thereof communicates with the outside of the sensor via the diffusion-limited layer 13.

<Configuration of Pump Cell>

The pump electrodes 15A and 15B are electrodes formed of platinum group elements such as platinum and rhodium or an alloy thereof. The electrode 15A is positioned on a wall face of one side of the solid electrolyte layer 11B (that is, a wall face of the layer 11B which forms the interior space 18) and the electrode 15B is positioned on a wall face of the other side of the solid electrolyte layer 11B (that is, a wall face of the layer 11B which forms the second atmospheric air introduction passage 17B). The electrodes 15A and 15B and the layer 11B configure the pump cell 15. The sensor 10 is configured to be able to apply a voltage from the pump cell voltage source 15C to the pump cell 15 (in particular, between the electrodes 15A and 15B). It should be noted that the electrode 15A is a cathode side electrode and the electrode 15B is an anode side electrode.

<Function of Pump Cell>

When a voltage is applied to the pump cell 15 and the oxygen in the interior space 18 contacts the pump electrode 15A, this oxygen becomes an oxygen ion on the electrode 15A and then, this oxygen ion moves toward the pump electrode 15B through the interior of the solid electrolyte layer 11B. At this time, an electric current proportional to the amount of the oxygen ion, which has moved through the interior of the solid electrolyte layer 11B, is generated between the electrodes 15A and 15B. Then, when the oxygen ion reaches the electrode 15B, the oxygen ion becomes the oxygen on the electrode 15B and then, is discharged to the second atmospheric air introduction passage 17B. That is, the pump cell 15 can discharge the oxygen included in the exhaust gas from the exhaust gas to the atmosphere by the pumping action and thereby, can lower the concentration of the oxygen included in the exhaust gas. The ability of the pumping action of the pump cell 15 increases as the voltage applied from the pump cell voltage source 15C to the pump cell 15 increases.

<Configuration of Sensor Cell>

The sensor electrodes 16A and 16B are electrodes formed of platinum group elements such as platinum and rhodium or an alloy thereof. The electrode 16A is positioned on a wall face of one side of the solid electrolyte layer 11A (that is, a wall face of the layer 11A which forms the interior space 18) and the electrode 16B is positioned on a wall face of the other side of the solid electrolyte layer 11A (that is, a wall face of the layer 11A which forms the first atmospheric air introduction passage 17A). The electrodes 16A and 16B and the layer 11A configure the sensor cell 16. The sensor 10 is configured to be able to apply a voltage from the sensor cell voltage source 16C to the sensor cell 16 (in particular, between the electrodes 16A and 16B). It should be noted that the electrode 16A is a cathode side electrode and the electrode 16B is an anode side electrode.

<Function of Sensor Cell>

When a voltage is applied to the sensor cell 16 and the SOx in the interior space 18 contacts the sensor electrode 16A, this SOx is dissolved on the electrode 16A, the oxygen of the SOx becomes an oxygen ion and then, this oxygen ion moves toward the sensor electrode 16B through the interior of the solid electrolyte layer 11A. At this time, an electric current proportional to the amount of the oxygen ion, which has moved through the interior of the layer 11A, is generated between the electrodes 16A and 16B. Then, when the oxygen ion reaches the electrode 16B, the oxygen ion becomes the oxygen on the electrode 16B and then, is discharged to the first atmospheric air introduction passage 17A.

<Air-Fuel Ratio Detecting Function 1 of 2 Cell Type Limiting Current Type Sensor>

Figure 2:
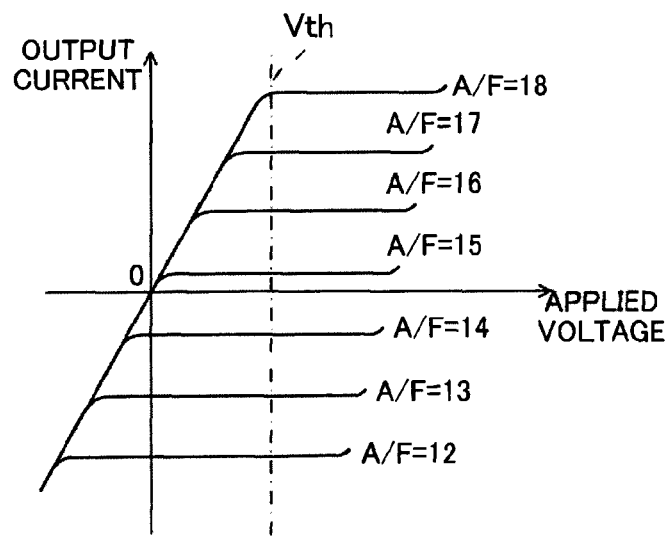
FIG. 2 shows an output property of the limiting current type sensor shown in FIG. 1.

FIG. 2 shows a relationship between the pump cell applied voltage and the pump cell output current in the 2 cell type limiting current sensor according to the first embodiment. The pump cell applied voltage is a voltage applied to the pump cell 15 by the pump cell voltage source 15C and the pump cell output current is an electric current flowing between the pump electrodes 15A and 15B. Further, in FIG. 2, a line indicated by A/F=12 shows a change of the output current relative to a change of the pump cell applied voltage in case that the air-fuel ratio of the exhaust gas is 12 and similarly, lines indicated by A/F=13 to A/F=18 show changes of the output currents relative to the changes of the pump cell applied voltages in case that the air-fuel ratios of the exhaust gas are 13 to 18, respectively.

As shown in FIG. 2, for example, in case that the air-fuel ratio of the exhaust gas is 18 and the pump cell applied voltage is within a range lower than a certain value Vth, when the pump cell output current is a negative value, an absolute value of the pump cell output current decreases as the pump cell applied voltage increases and when the pump cell output current is a positive value, the absolute value of the pump cell output current increases as the pump cell applied voltage increases. Further, in case that the pump cell applied voltage is within a constant range higher than or equal to the certain value Vth, the pump cell output current is a constant value independently of the pump cell applied voltage.

Similarly, this relationship between the pump cell applied voltage and the pump cell output current is established in case that the air-fuel ratio of the exhaust gas is 12 to 17. In this regard, as understood from FIG. 2, in all of the air-fuel ratios to be detected, when applying a voltage in which the pump cell output current is constant independently of the pump cell applied voltage to the pump cell 15, the air-fuel ratio of the exhaust gas can be detected on the basis of the detected pump cell output current. That is, the 2 cell type limiting current type sensor 10 according to the first embodiment can be used for detecting the air-fuel ratio of the exhaust gas. It should be noted that the air-fuel ratio of the exhaust gas is a parameter having a correlation with the concentration of the oxygen included in the exhaust gas and therefore, in principle, the 2 cell type limiting current type sensor according to the first embodiment can detect the concentration of the oxygen included in the exhaust gas.

<Air-Fuel Ratio Detecting Function 2 of 2 Cell Type Limiting Current Type Sensor>

Further, the relationship between the sensor cell applied voltage and the sensor cell output current in the 2 cell type limiting current type sensor according to the first embodiment is the same as that shown in FIG. 2. Therefore, under the condition where the pump cell applied voltage is zero (that is, the pump cell 15 does not function), in all of the air-fuel ratios to be detected, when applying a voltage in which the sensor cell output current is constant independently of the sensor cell applied voltage to the sensor cell 16, the air-fuel ratio of the exhaust gas can be detected on the basis of the detected sensor cell output current. That is, the 2 cell type limiting current type sensor 10 according to the first embodiment can be used for detecting the air-fuel ratio of the exhaust gas. It should be noted that the sensor cell applied voltage is a voltage applied to the sensor cell 16 by the sensor cell voltage source 16C and the sensor cell output current is an electric current flowing between the sensor electrodes 16A and 16B.

<Output Property of 2 Cell Type Limiting Current Type Sensor>

From the study of the inventors of this application, it has been newly realized that an electric current corresponding to the concentration of the SOx included in the exhaust gas can be obtained from the limiting current type sensor by lowering the voltage applied to the 2 cell type limiting current type sensor (in particular, the voltage applied from the sensor cell voltage source 16C to the sensor cell 16) from a predetermined voltage. Next, this will be described. It should be noted that in the following description, an output current is an electric current output from the sensor cell 16.

Figure 3:
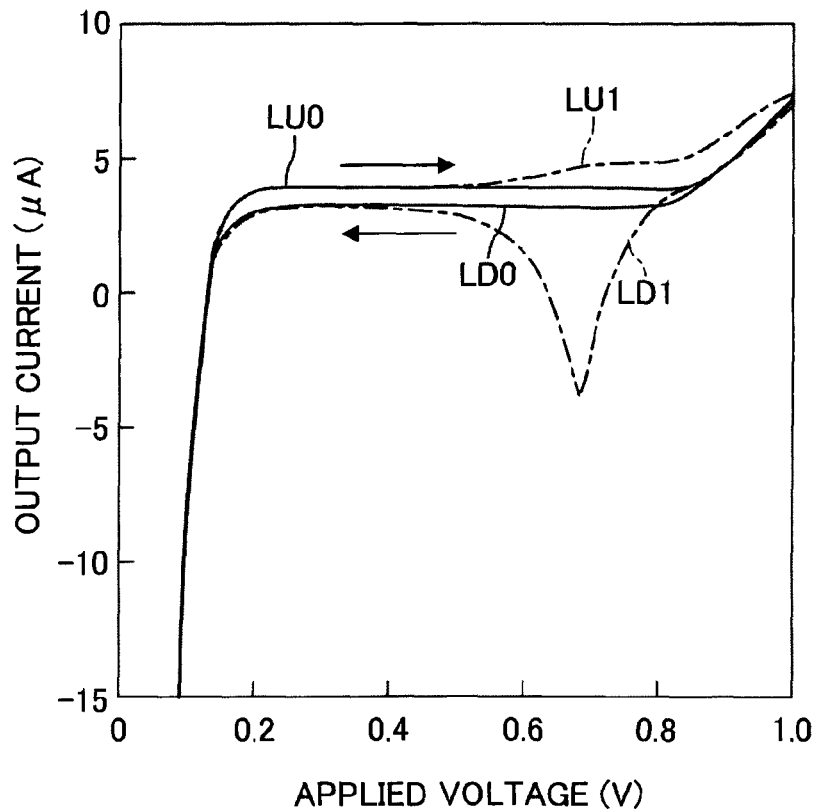
FIG. 3 shows an output property of the limiting current type sensor shown in FIG. 1.

In FIG. 3, shown is a change of the output current while gradually raising the applied voltage from 0.1V to 1.0V and then, gradually lowering the applied voltage from 1.0V to 0.1V. The abscissa axis of FIG. 3 indicates the applied voltage and the longitudinal axis of FIG. 3 indicates the output current. It should be noted that a voltage for lowering the concentration of the oxygen included in the exhaust gas in the interior space 18 to zero (or generally zero) is applied to the pump cell 15 while changing the applied voltage.

In FIG. 3, the solid line LU0 indicates a change of the output current while raising the applied voltage from 0.1V to 1.0V in case that no SOx is included in the exhaust gas (that is, the concentration of the SOx included in the exhaust gas is zero) and the solid line LD0 indicates a change of the output current while lowering the applied voltage from 1.0V to 0.1V in case that no SOx is included in the exhaust gas. In FIG. 3, the chain line LU1 indicates a change of the output current while raising the applied voltage from 0.1V to 1.0V in case that the SOx is included in the exhaust gas and the chain line LD1 indicates a change of the output current while lowering the applied voltage from 1.0V to 0.1V in case that the SOx is included in the exhaust gas.

In case that no SOx is included in the exhaust gas, when the applied voltage is raised from 0.1V to about 0.2V, as shown by the solid line LU0 in FIG. 3, the output current increases rapidly to about 4 microampere. Then, while the applied voltage is raised from about 0.2V to about 0.85V, the output current is generally constant at about 4 microampere. Then, when the applied voltage exceeds about 0.85V, the output current starts to increase. Then, while the applied voltage is raised from about 0.85V to 1.0V, the output current gradually increases and when the applied voltage reaches 1.0V, the output current reaches about 7 microampere.

Thereafter, when the applied voltage is gradually lowered from 1.0V toward 0.4V, as shown by the solid line LD0 in FIG. 3, the output current gradually decreases from about 7 microampere and while the applied voltage falls below about 0.85V and then, reaches 0.4V, the output current is generally constant at about 3.5 microampere.

On the other hand, in case that the SOx is included in the exhaust gas, when the applied voltage is raised from 0.1V to about 0.2V, as shown by the chain line LU1 in FIG. 3, the output current increases rapidly to about 4 microampere. Then, while the applied voltage is raised from about 0.2V to about 0.6V, the output current is generally constant at about 4 microampere. Then, when the applied voltage exceeds about 0.6V, the output current starts to increase. Then, while the applied voltage is raised from about 0.6V to 1.0V, the output current gradually increases and when the applied voltage reaches 1.0V, the output current reaches about 7 microampere.

Thereafter, when the applied voltage is gradually lowered from 1.0V toward 0.4V, as shown by the chain line LD1 in FIG. 3, the output current gradually decreases from about 7 microampere and while the applied voltage falls below about 0.8V and then, reaches about 0.7V, the output current rapidly decreases, the direction of the flow of the output current reverses and then, the output current reaches about −5 microampere. Then, while the applied voltage is further lowered from about 0.7V to 0.4V, the output current rapidly increases and the direction of the flow of the output current returns to the original direction and when the applied voltage reaches 0.4V, the output current becomes about 3.5 microampere.

Therefore, in case that the SOx is included in the exhaust gas, when the applied voltage is raised from 0.4V to 0.8V and then, the applied voltage is lowered from 0.8V to 0.4V, the output current rapidly decreases and then, rapidly increases while the applied voltage is lowered. That is, when the applied voltage is lowered from 0.8V to 0.4V, the output current changes so as to have a minimum value (that is, a peak value). In this regard, when the applied voltage reaches about 0.7V, the output current becomes the peak value.

It should be noted that the output current while the applied voltage exceeds about 0.6V and then, reaches 1.0V in case that the SOx is included in the exhaust gas is larger than that while the applied voltage exceeds about 0.6V and then, reaches 1.0V in case that no SOx is included in the exhaust gas.

<Advantage of 2 Cell Type Limiting Current Type Sensor According to the First Embodiment>

Figure 4:
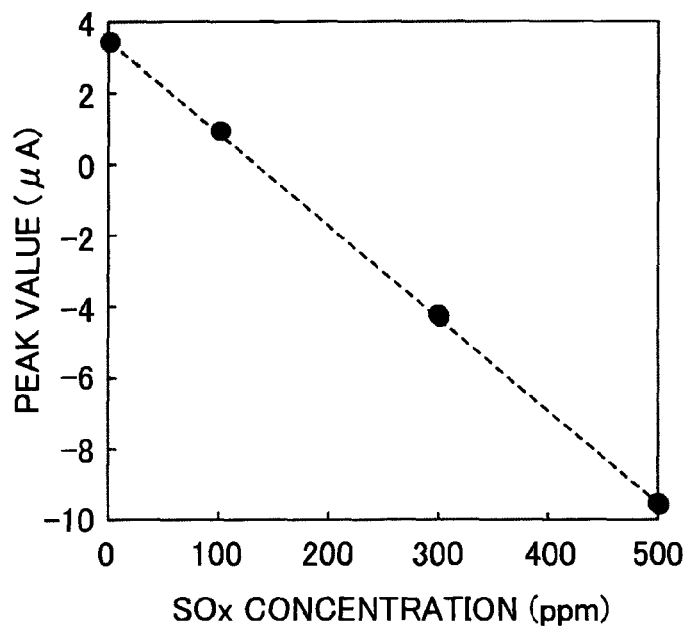
FIG. 4 shows a relationship between a SOx concentration and a peak value of an output current.

From the study of the inventors of this application, it has been realized that in the 2 cell type limiting current type sensor, a relationship shown in FIG. 4 exists between the peak value of the output current and the SOx concentration while lowering the applied voltage from 0.8V to 0.4V as described above. That is, it has been realized that the concentration of the SOx included in the exhaust gas increases as the difference between a reference current (that is, the output current when the applied voltage reaches 0.8V) and the peak value increases. Further, the 2 cell type limiting current type sensor according to the first embodiment can be used for detecting the concentration of the oxygen included in the exhaust gas (as a result, the air-fuel ratio of the exhaust gas). Therefore, by using the 2 cell type limiting current type sensor, which can be used for detecting the concentration of the oxygen included in the exhaust gas, according to the first embodiment, the SOx concentration can be calculated (detected) on the basis of the peak value.

<Configuration of 1 Cell Type Limiting Current Type Sensor>

Figure 5:
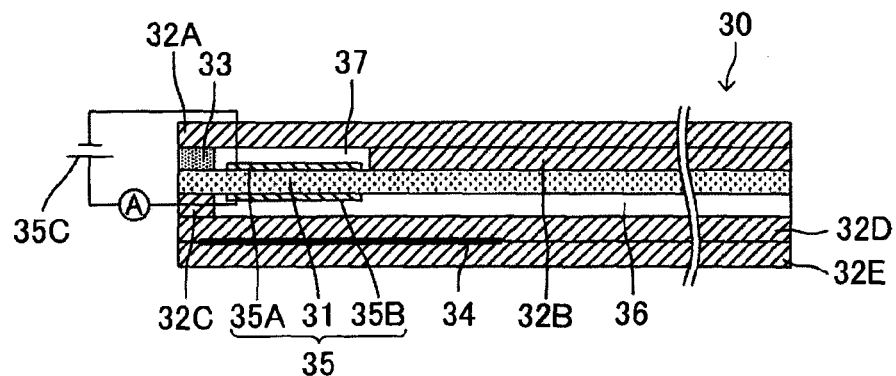
FIG. 5 shows another embodiment of the limiting current type sensor of the invention (1 cell type limiting current type sensor).

A limiting current type sensor according to the first embodiment of the invention is shown in FIG. 5. The limiting current type sensor shown in FIG. 5 is a 1 cell type limiting current type sensor. In FIG. 5, 30 denotes the limiting current type sensor, 31 denotes a solid electrolyte layer, 32A denotes a first alumina layer, 32B denotes a second alumina layer, 32C denotes a third alumina layer, 32D denotes a fourth alumina layer, 32E denotes a fifth alumina layer, 33 denotes a diffusion-limited layer, 34 denotes a heater, 35 denotes a sensor cell, 35A denotes a first sensor electrode, 35B denotes a second sensor electrode, 35C denotes a sensor cell voltage source, 36 denotes an atmospheric air introduction passage and 37 denotes an interior space.

The solid electrolyte layer 31 is a layer formed of zirconia or the like and have an oxygen ion conductive property. The alumina layers 32A to 32E are layers formed of alumina. The diffusion-limited layer 33 is a porous layer which can pass the exhaust gas therethrough. In the sensor 30, the layers are laminated such that the fifth alumina layer 32E, the fourth alumina layer 32D, the third alumina layer 32C, the solid electrolyte layer 31, the diffusion-limited layer 33 and the second alumina layer 32B and the first alumina layer 32A are positioned in order from the lower side of FIG. 5. The heater 34 is positioned between the fourth and fifth alumina layers 32D and 32E.

The atmospheric air introduction passage 36 is a space formed by the solid electrolyte layer 31 and the third and fourth alumina layers 32C and 32D and a part thereof opens to the atmosphere. The interior space 37 is a space formed by the first alumina layer 32A, the solid electrolyte layer 31, the diffusion-limited layer 33 and the second alumina layer 32B and a part thereof communicates with the outside of the sensor via the diffusion-limited layer 33.

<Configuration of Sensor Cell>

The sensor electrodes 35A and 35B are electrodes formed of platinum group elements such as platinum and rhodium or an alloy thereof. The electrode 35A is positioned on a wall face of one side of the solid electrolyte layer 31 (that is, a wall face of the layer 31 which forms the interior space 37) and the electrode 35B is positioned on a wall face of the other side of the solid electrolyte layer 31 (that is, a wall face of the layer 31 which forms the atmospheric air introduction passage 36). The electrodes 35A and 35B and the layer 31 configure the sensor cell 35. The sensor 30 is configured to be able to apply a voltage from the sensor cell voltage source 35C to the sensor cell 35 (in particular, between the electrodes 35A and 35B). It should be noted that the electrode 35A is a cathode side electrode and the electrode 35B is an anode side electrode.

<Function of Sensor Cell>

When a voltage is applied to the sensor cell 35 and the SOx in the interior space 37 contacts the sensor electrode 35A, this SOx is dissolved on the electrode 35A, the oxygen of the SOx becomes an oxygen ion and then, this oxygen ion moves toward the electrode 35B through the interior of the layer 31. At this time, an electric current proportional to the amount of the oxygen ion, which has moved through the interior of the layer 31, is generated between the electrodes 35A and 35B. Then, when the oxygen ion reaches the electrode 35B, the oxygen ion becomes the oxygen on the electrode 35B and then, is discharged to the atmospheric air introduction passage 36.

<Air-Fuel Ratio Detecting Function of 1 Cell Type Limiting Current Type Sensor>

The relationship between the sensor cell applied voltage and the sensor cell output current in the 1 cell type limiting current type sensor according to the first embodiment is the same as that shown in FIG. 2. Therefore, in all of the air-fuel ratios to be detected, when applying a voltage in which the sensor cell output current is constant independently of the sensor cell applied voltage to the sensor cell 35, the air-fuel ratio of the exhaust gas can be detected on the basis of the detected sensor cell output current. That is, the 1 cell type limiting current type sensor 30 according to the first embodiment can be used for detecting the air-fuel ratio of the exhaust gas. It should be noted that the air-fuel ratio of the exhaust gas is a parameter having a correlation with the concentration of the oxygen included in the exhaust gas and therefore, in principle, the 1 cell type limiting current type sensor according to the first embodiment can detect the concentration of the oxygen included in the exhaust gas. Further, the sensor cell applied voltage is a voltage applied to the sensor cell 35 by the sensor cell voltage source 35C and the sensor cell output current is an electric current flowing between the sensor electrodes 35A and 35B.

<Output Property of 1 Cell Type Limiting Current Type Sensor>

From the study of the inventors of this application, it has been realized that similar to the 2 cell type limiting current type sensor, an electric current corresponding to the concentration of the SOx included in the exhaust gas can be obtained from the limiting current type sensor by lowering the voltage applied to the 1 cell type limiting current type sensor (in particular, the voltage applied from the sensor cell voltage source 35C to the sensor cell 35) from a predetermined voltage. Next, this will be described. It should be noted that in the following description, an output current is an electric current output from the sensor cell 35 and the concentration of the oxygen included in the exhaust gas is constant at 1 percent.

Figure 6:
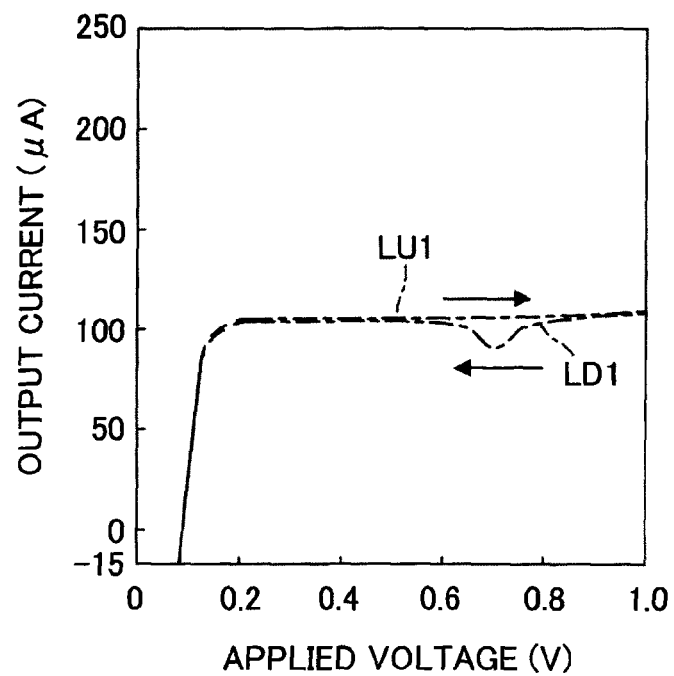
FIG. 6 shows an output property of the limiting current type sensor shown in FIG. 5.

In FIG. 6, shown is a change of the output current while gradually raising the applied voltage from 0.1V to 1.0V and then, gradually lowering the applied voltage from 1.0V to 0.1V. The abscissa axis of FIG. 6 indicates the applied voltage and the longitudinal axis of FIG. 6 indicates the output current.

In FIG. 6, the chain line LU1 indicates a change of the output current while raising the applied voltage from 0.1V to 1.0V in case that the SOx is included in the exhaust gas and the chain line LD1 indicates a change of the output current while lowering the applied voltage from 1.0V to 0.1V in case that the SOx is included in the exhaust gas.

In case that the SOx is included in the exhaust gas, when the applied voltage is raised from 0.1V to about 0.2V, as shown by the chain line LU1 in FIG. 6, the output current increases rapidly to about 100 microampere. Then, while the applied voltage is raised from about 0.2V to about 0.6V, the output current is generally constant at about 100 microampere. Then, when the applied voltage exceeds about 0.6V, the output current starts to increase. Then, while the applied voltage is raised from about 0.6V to 1.0V, the output current slightly gradually increases and when the applied voltage reaches 1.0V, the output current reaches about 105 microampere.

Thereafter, when the applied voltage is gradually lowered from 1.0V toward 0.4V, as shown by the chain line LD1 in FIG. 6, the output current gradually decreases from about 105 microampere and while the applied voltage falls below about 0.8V and then, reaches about 0.7V, the output current rapidly decreases and then, the output current reaches about 80 microampere. Then, while the applied voltage is lowered from about 0.7V to 0.4V, the output current rapidly increases and when the applied voltage reaches 0.4V, the output current becomes about 100 microampere.

Therefore, in case that the SOx is included in the exhaust gas, when the applied voltage is raised from 0.4V to 0.8V and then, the applied voltage is lowered from 0.8V to 0.4V, the output current rapidly decreases and then, rapidly increases while the applied voltage is lowered. That is, when the applied voltage is lowered from 0.8V to 0.4V, the output current changes so as to have a minimum value (that is, a peak value). In this regard, when the applied voltage reaches about 0.7V, the output current becomes the peak value.

<Advantage of 1 Cell Type Limiting Current Type Sensor According to the First Embodiment>

From the study of the inventors of this application, it has been realized that in the 1 cell type limiting current type sensor, a relationship similar to that shown in FIG. 4 exists between the peak value of the output current and the SOx concentration while lowering the applied voltage from 0.8V to 0.4V as described above. That is, it has been realized that the concentration of the SOx included in the exhaust gas increases as the difference between a reference current (that is, the output current when the applied voltage reaches 0.8V) and the peak value increases. Further, the 1 cell type limiting current type sensor according to the first embodiment can be used for detecting the concentration of the oxygen included in the exhaust gas (as a result, the air-fuel ratio of the exhaust gas). Therefore, by using the 1 cell type limiting current type sensor, which can be used for detecting the concentration of the oxygen included in the exhaust gas, according to the first embodiment, the SOx concentration can be calculated (detected) on the basis of the peak value.

<SOx Concentration Detection Device According to the First Embodiment>

Figure 7:
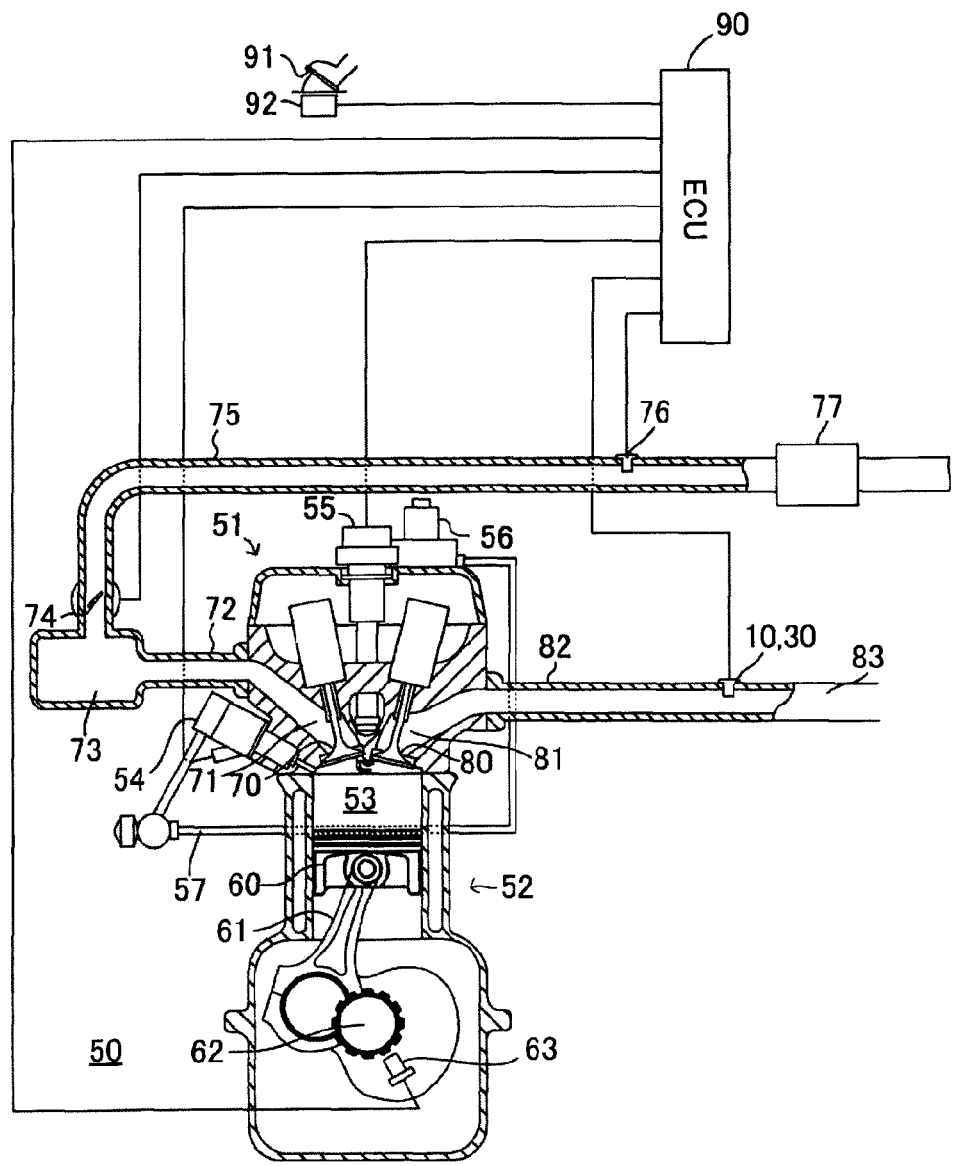
FIG. 7 shows an internal combustion engine comprising a SOx concentration detection device having the limiting current type sensor shown in FIG. 1 or 5.

In FIG. 7, an internal combustion engine comprising a SOx concentration detection device having the limiting current type sensor 10 or 30 shown in FIG. 1 or 5 is shown. The engine shown in FIG. 7 is a spark ignition type internal combustion engine (so-called gasoline engine). However, the invention can be applied to a compression self-ignition type internal combustion engine (so-called diesel engine). Further, the engine shown in FIG. 7 is operated at a stoichiometric air-fuel ratio (stoich) in a substantial engine operation area.

<Configuration of Engine>

In FIG. 7, 10 or 30 denotes the limiting current type sensor shown in FIG. 1 or 5, 50 denotes a body of the engine, 51 denotes a cylinder head, 52 denotes a cylinder block, 53 denotes a combustion chamber, 54 denotes a fuel injector, 55 denotes a spark plug, 56 denotes a fuel pump, 57 denotes a fuel supply pipe, 60 denotes a piston, 61 denotes a connecting rod, 62 denotes a crank shaft, 63 denotes a crank angle sensor, 70 denotes an intake valve, 71 denotes an intake port, 72 denotes an intake manifold, 73 denotes a surge tank, 74 denotes a throttle valve, 75 denotes an intake pipe, 76 denotes an air flow meter, 77 denotes an air filter, 80 denotes an exhaust valve, 81 denotes an exhaust port, 82 denotes an exhaust manifold, 83 denotes an exhaust pipe, 90 denotes an electronic control unit (ECU), 91 denotes an acceleration pedal and 92 denotes an acceleration pedal depression amount sensor.

<Configuration/Function of ECU>

The fuel injector 54, the spark plug 55, the throttle valve 74, the crank angle sensor 63, the air flow meter 76, the acceleration pedal depression amount sensor 92 and the limiting current type sensor 10 or 30 are electrically connected to the ECU 90. The ECU 90 sends signals for operating the fuel injector 54, the spark plug 55 and the throttle valve 74 thereto. Further, the ECU 90 receives signals from the crank angle sensor 63, the air flow meter 76 and the acceleration pedal depression amount sensor 92. A signal corresponding to a rotation speed of the crank shaft 62 is output from the crank angle sensor 63. The ECU 90 calculates an engine speed on the basis of the signal received from the crank angle sensor 63. A signal corresponding to a flow rate of an air passing through the air flow meter (that is, a flow rate of the air suctioned into the combustion chamber 53) is output from the air flow meter 76. The ECU 90 calculates an intake air amount on the basis of the signal received from the air flow meter 76. A signal corresponding to a depression amount of the acceleration pedal 91 is output from the acceleration pedal depression amount sensor 92.

The ECU 90 calculates an engine load on the basis of the signal received from the acceleration pedal depression amount sensor 92.

<Limiting Current Type Sensor>

The limiting current type sensor 10 or 30 is mounted on the exhaust pipe 83. Therefore, a gas, which is an object to be detected by the limiting current type sensor 10 or 30 (that is, a gas to be detected) is an exhaust gas discharged from the combustion chamber 53. An electric current corresponding to the concentration of the SOx included in the exhaust gas, which reaches the limiting current type sensor, is output from the limiting current type sensor 10 or 30. The ECU 90 calculates the SOx concentration on the basis of the current received from the limiting current type sensor 10 or 30 (the detail of this calculation method will be described later).

<SOx Concentration Detection According to the First Embodiment>

Figure 8:
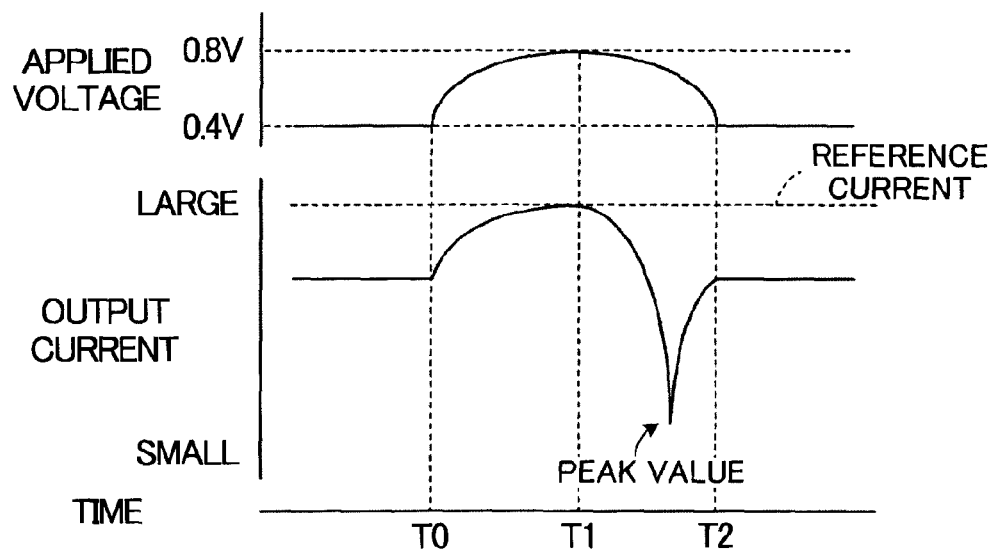
FIG. 8 shows a time chart showing the output current corresponding to a change of an applied voltage according to the first embodiment.

With reference to FIG. 8, the SOx concentration detection according to the first embodiment will be described. According to the first embodiment, the applied voltage is constantly maintained at 0.4V (refer to a period before a time T0 shown in FIG. 8). That is, the voltage of 0.4V is constantly applied to the sensor. Then, in the SOx concentration detection according to the first embodiment, the applied voltage is raised from 0.4V to 0.8V (refer to a period from the time T0 to a time T1 shown in FIG. 8) and then, the applied voltage is lowered from 0.8V to 0.4V (refer to a period from the time T1 to a time T2 shown in FIG. 8). At this time, the ECU calculates (that is, detects) the SOx concentration by using the reference current and the peak value of the output current input to the ECU while the applied voltage is lowered from 0.8V to 0.4V. At this time, the calculated SOx concentration increases as the difference between the reference current and the peak value increases.

It should be noted that in case that the SOx concentration is calculated by using the difference between the peak value and the reference current (hereinafter, this difference will be referred to as "current difference"), for example, the SOx concentration corresponding to the current difference is previously obtained every the current difference by an experiment or the like, these obtained SOx concentrations are memorized in the ECU in the form of a map as a function of the current difference and the SOx concentration is calculated by reading out the SOx concentration corresponding to the current difference calculated during the detection of the SOx concentration from the map.

<Advantage of SOx Concentration Detection Device According to the First Embodiment>

The limiting current type sensor of the SOx concentration detection device according to the first embodiment can be used for detecting the concentration of the oxygen included in the exhaust gas (as a result, the air-fuel ratio of the exhaust gas). Therefore, according to the SOx concentration detection device according to the first embodiment, the concentration of the SOx included in the exhaust gas can be detected by using the sensor which can be used for detecting the concentration of the oxygen included in the exhaust gas. That is, the inventors of this application have realized that the influence of the SOx occupying the output current when the applied voltage is maintained at a constant voltage (for example, 0.4V) or the influence of the SOx occupying the output current when the applied voltage is raised is smaller than that of the other component (for example, $O_2$ and NOx) occupying the output current and on the other hand, the influence of the SOx occupying the output current when the applied voltage is lowered from a predetermined voltage (for example, 0.8V) is larger than that of the other component occupying the output current and thus, according to the SOx concentration detection device according to the first embodiment, the SOx concentration can be detected accurately by using the sensor which can be used for detecting the concentration of the oxygen included in the exhaust gas.

Further, the peak value is an output current which is an output current during the lowering of the applied voltage and is different most considerably from the output current in case that the SOx concentration is zero. Therefore, the peak value is an output current accurately corresponding to the SOx concentration. Thus, the SOx concentration can be detected more accurately by using the peak value as the output current for the SOx concentration detection.

Further, according to the first embodiment, the voltage, which is applied to the sensor prior to the start of the lowering of the applied voltage, is 0.4V. Therefore, this voltage is lower than 0.8V, which is applied when the lowering of the applied voltage is started. Thus, according to the first embodiment, comparing with the case that the voltage, which is applied to the sensor prior to the start of the lowering of the applied voltage, is equal to 0.8V, the electric power consumed by the SOx concentration detection can be decreased.

<Application Range of the First Embodiment>

It should be noted that in the SOx concentration detection according to the first embodiment, the applied voltage when the raising of the applied voltage is started (that is, the voltage constantly applied to the sensor) is not limited to 0.4V and may be any voltages for generating a change of the output current having the peak value while lowering the applied voltage after raising the applied voltage, for example, a voltage lower than or equal to 0.6V, preferably, a voltage equal to 0.4V.

Further, the applied voltage when the raising of the applied voltage is ended is not limited to 0.8V and may be any voltages for generating a change of the output current having the peak value while lowering the applied voltage after raising the applied voltage or any voltages higher than or equal to a maximum voltage of an output stabilizing voltage range (that is, a range in which the output current is generally constant independently of the applied voltage in case that the SOx concentration is zero, for example, a range from 0.2V to 0.8V), for example, a voltage higher than 0.8V.

Further, the applied voltage when the lowering of the applied voltage is ended is not limited to 0.4V and may be any voltages lower than or equal to a voltage corresponding to the peak value, for example, a voltage lower than or equal to 0.7V, preferably, a voltage equal to 0.4V. Therefore, the applied voltage when the raising of the applied voltage is started may be the same or different from that when the lowering of the applied voltage is ended.

Furthermore, in the SOx concentration detection according to the first embodiment, the peak value is used, however, in place of this peak value, an output current within a range of the output current rapidly decreasing or increasing while the applied voltage is lowered from 0.8V to 0.4V may be used.

<Reference Current>

It should be noted that the concentration of the oxygen included in the exhaust gas flowing into the interior space of the sensor may change during lowering the applied voltage. In this case, the output current when the applied voltage is 0.8V indicates the concentration of the oxygen before it changes while the output current when the applied voltage is 0.4V indicates the concentration of the oxygen after it changes. Therefore, the output current when the applied voltage is 0.4V more accurately reflects the concentration of the oxygen included in the exhaust gas in the interior space of the sensor when the peak value is output, comparing with the output current when the applied voltage is 0.8V. Accordingly, in the SOx concentration detection according to the first embodiment, in case that the applied voltage is lowered from 0.8V to 0.4V, in place of the reference current, the output current at the time of the applied voltage reaching 0.4V (or the output current after a predetermined time has elapsed from that time) may be used as the reference current. According to this, even when the concentration of the oxygen included in the exhaust gas changes during the lowering of the applied voltage, the SOx concentration can be detected accurately.

Further, in the first embodiment, in place of using the peak value and the reference current to calculate the SOx concentration, the peak value and a conversion coefficient may be used to calculate the SOx concentration. In this regard, the calculated SOx concentration increases as the peak value increases toward the negative value. That is, when the peak value is negative, the calculated SOx concentration increases as the absolute value of the peak value increases and when the peak value is positive, the calculated SOx concentration increases as the absolute value of the peak value decreases. It should be noted that the conversion coefficient is a coefficient for converting the peak value to the SOx concentration according to the relationship shown in FIG. 4. Of course, in case that the peak value occurs as a positive value, the calculated SOx concentration increases as the peak value increases toward the positive value.

<Sweep Speed According to the First Embodiment>

In the SOx concentration detection according to the first embodiment, if a speed of the raising or lowering of the applied voltage (a sweep speed) is too high, no peak value may be output or the peak value sufficiently corresponding to the SOx concentration may not be output when the applied voltage is lowered. Accordingly, in the SOx concentration detection according to the first embodiment, it is preferred that the speeds of the raising and lowering of the applied voltage, in which the peak value sufficiently corresponding to the SOx concentration is output while the applied voltage is lowered, are selected.

Figure 9A:
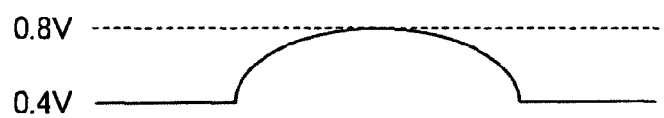
FIG. 9A shows a manner of the raising and lowering of the applied voltage.
Figure 9B:
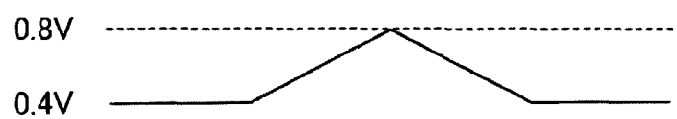
FIG. 9B shows another manner of the raising and lowering of the applied voltage.

In particular, as shown in FIG. 9A, it is preferred that the applied voltage is raised such that the raising speed of the applied voltage gradually decreases and then, the applied voltage is lowered such that the lowering speed of the applied voltage gradually increases. Otherwise, as shown in FIG. 9B, it is preferred that the applied voltage is raised such that the raising speed of the applied voltage is maintained at a constant speed and then, the applied voltage is lowered such that the lowering speed of the applied voltage is maintained at a constant speed.

Further, in particular, in the SOx concentration detection according to the first embodiment, when expressing the change of the applied voltage while the applied voltage is raised from 0.4V to 0.8V and then, the applied voltage is lowered from 0.8V to 0.4V by a frequency, it is preferred that the frequency is smaller than or equal to 100 Hz. In other words, it is preferred that the time necessary from the start of the raising of the applied voltage to the end of the lowering of the applied voltage is longer than or equal to 0.01 seconds.

<Configuration 1 of SOx Detection Electric Circuit>

Figure 10A:
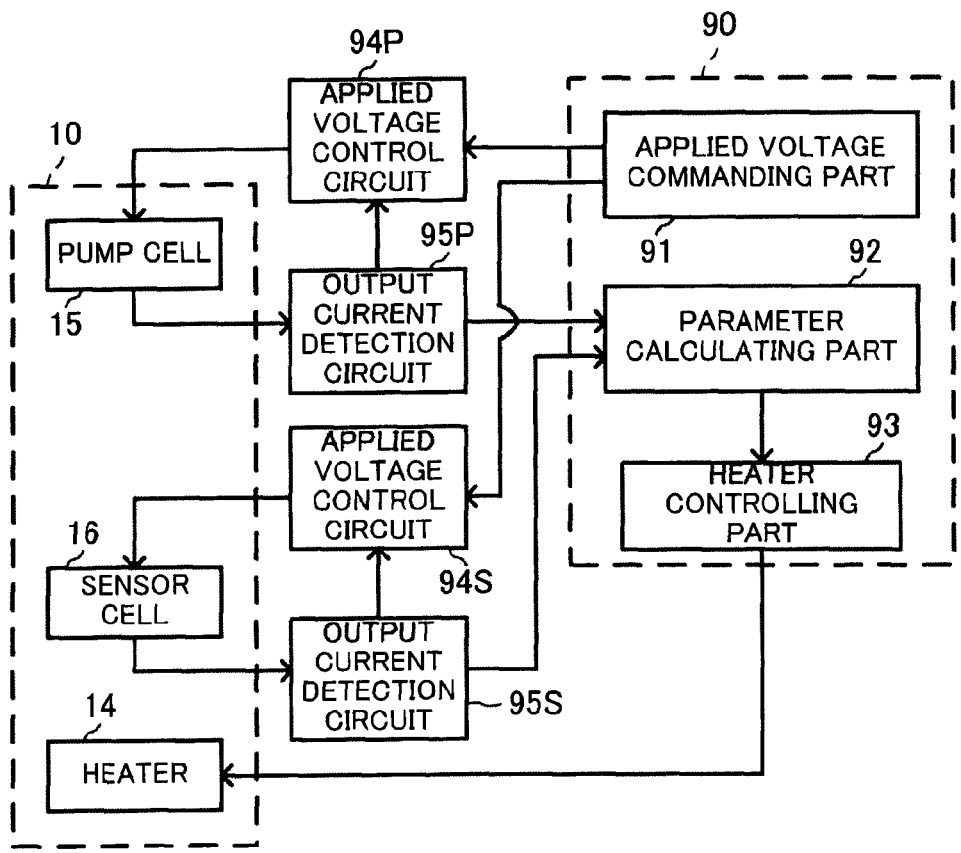
FIG. 10A shows an example of an electric circuit employed in the limiting current type sensor shown in FIG. 1.

It should be noted that in case that the engine comprises the limiting current type sensor (2 cell type limiting current type sensor) shown in FIG. 1, as a SOx detection electric circuit, for example, an electric circuit shown in FIG. 10A is employed. In FIG. 10A, 10 denotes the limiting current type sensor (that is, the limiting current type sensor shown in FIG. 1), 14 denotes the heater, 15 denotes the pump cell, 16 denotes the sensor cell, 90 denotes the ECU, 91 denotes an applied voltage commanding part, 92 denotes a parameter calculating part, 93 denotes a heater controlling part, 94P and 94S denote applied voltage control circuit, respectively and 95P and 95S denote output current detection circuit, respectively.

The applied voltage commanding part 91, the parameter calculating part 92 and the heater controlling part 93 are elements of the ECU 90.

The applied voltage commanding part 91 sends a command relating to the voltage applied to the pump cell 15 to the applied voltage control circuit 94P and send a command relating to the voltage applied to the sensor cell 16 to the applied voltage control circuit 94S.

The parameter calculating part 92 receives a signal corresponding to the pump cell output current from the output current detection circuit 95P, calculates the pump cell output current on the basis of this received signal and calculates the air-fuel ratio of the exhaust gas (or the concentration of the oxygen included in the exhaust gas) on the basis of this calculated output current. The parameter calculating part 92 receives a signal corresponding to the sensor cell output current from the output current detection circuit 95S, calculates the sensor cell output current on the basis of this received signal and calculates the concentration of the SOx included in the exhaust gas on the basis of this calculated output current. Further, the parameter calculating part 92 calculates an impedance of the circuit in the sensor 10 on the basis of the signals received from the output current detection circuit 95P and 95S and sends information relating to this calculated impedance to the heater controlling part 93. The heater controlling part 93 sends to the heater 14, a control signal for controlling the heater 14 on the basis of the information relating to the impedance received from the parameter calculating part 92.

The applied voltage control circuit 94P controls the pump cell applied voltage on the basis of the command received from the applied voltage commanding part 91 (or on the basis of the command received from the applied voltage commanding part 91 and the signal corresponding to the pump cell output current provided from the output current detection circuit 95P).

The output current detection circuit 95P detects the pump cell output current and sends a signal corresponding to this detected output current to the parameter calculating part 92 and the applied voltage control circuit 94P.

The applied voltage control circuit 94S controls the sensor cell applied voltage on the basis of the command received from the applied voltage commanding part 91 (or the command received from the applied voltage commanding part 91 or the signal corresponding to the sensor cell output current provided from the output current detection circuit 95S).

The output current detection circuit 95S detects the sensor cell output current and sends a signal corresponding to this detected output current to the parameter calculating part 92 and the applied voltage control circuit 94S.

<Configuration 2 of SOx Detection Electric Circuit>

Figure 10B:
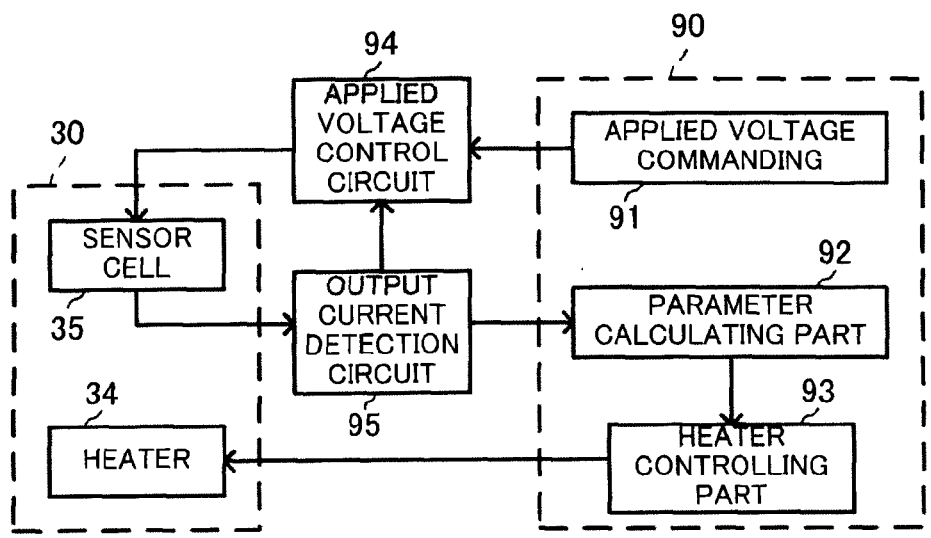
FIG. 10B shows an example of an electric circuit employed in the limiting current type sensor shown in FIG. 4.

In case that the engine comprises the limiting current type sensor (1 cell type limiting current type sensor) shown in FIG. 5, as a SOx detection electric circuit, for example, an electric circuit shown in FIG. 10B is employed. In FIG. 10B, 30 denotes the limiting current type sensor (that is, the limiting current type sensor shown in FIG. 5), 34 denotes the heater, 35 denotes the sensor cell, 90 denotes the ECU, 91 denotes an applied voltage commanding part, 92 denotes a parameter calculating part, 93 denotes a heater controlling part, 94 denotes an applied voltage control circuit and 95 denotes an output current detection circuit.

The applied voltage commanding part 91, the parameter calculating part 92 and the heater controlling part 93 are elements of the ECU 90.

The applied voltage commanding part 91 sends a command relating to the voltage applied to the sensor cell 35 to the applied voltage control circuit 94.

The parameter calculating part 92 receives a signal corresponding to the sensor cell output current from the output current detection circuit 95, calculates the sensor cell output current on the basis of this received signal and calculates the air-fuel ratio of the exhaust gas (or the concentration of the oxygen included in the exhaust gas) or the concentration of the SOx included in the exhaust gas on the basis of this calculated output current. Further, the parameter calculating part 92 calculates an impedance of the circuit in the sensor 30 on the basis of the signal received from the output current detection circuit 95 and sends information relating to this calculated impedance to the heater controlling part 93. The heater controlling part 93 sends to the heater 34, a control signal for controlling the heater 34 on the basis of the information relating to the impedance received from the parameter calculating part 92.

The applied voltage control circuit 94 controls the sensor cell applied voltage on the basis of the command received from the applied voltage commanding part 91 (or the command received from the applied voltage commanding part 91 or the signal corresponding to the sensor cell output current provided from the output current detection circuit 95).

The output current detection circuit 95 detects the sensor cell output current and sends a signal corresponding to this detected output current to the parameter calculating part 92 and the applied voltage control circuit 94.

<SOx Concentration Detection Flow>

An example of a flow of the aforementioned SOx concentration detection according to the first embodiment will be described. This flow is shown in FIG. 11.

Figure 11:
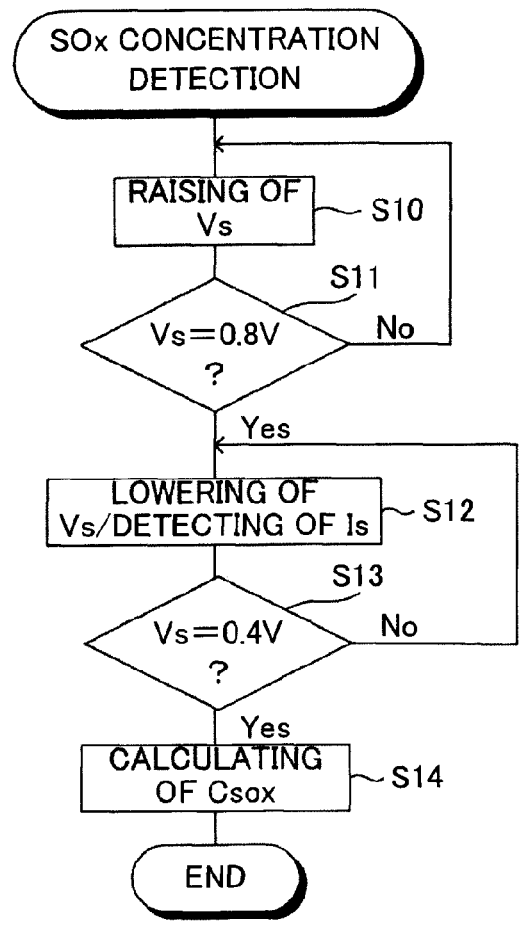
FIG. 11 shows an example of an embodiment of a SOx concentration detection flow according to the first embodiment.

When the flow shown in FIG. 11 starts, the applied voltage is maintained at 0.4V. Then, at the step 10, the applied voltage Vs is raised from 0.4V toward 0.8V. Next, at the step 11, it is judged if the applied voltage Vs reaches 0.8V (Vs=0.8V). In this regard, when it is judged that Vs=0.8V, the flow proceeds to the step 12. On the other hand, when it is not judged that Vs=0.8V, the flow returns to the step 10. Therefore, until it is judged that Vs=0.8V at the step 11, the raising of the applied voltage Vs is continued.

At the step 12, the applied voltage Vs is lowered from 0.8V toward 0.4V and the output current Is is detected. Next, at the step 13, it is judged if the applied voltage Vs reaches 0.4V (Vs=0.4V). In this regard, when it is judged that Vs=0.4V, the flow proceeds to the step 14. On the other hand, when it is not judged that Vs=0.4V, the flow returns to the step 12. Therefore, until it is judged that Vs=0.4V at the step 13, the lowering of the applied voltage Vs and the detecting of the output current Is are continued.

At the step 14, the SOx concentration Csox is calculated on the basis of the peak value of the output current Is detected at the step 12 and then, the flow ends.

<Sensor Element Temperature>

It should be noted that in the SOx concentration detection according to the aforementioned embodiment, the occurrence of the reaction relating to the SOx in the sensor cell is supposed to be a reason for the current corresponding to the SOx concentration being output from the sensor while the applied voltage is lowered. On the other hand, this reaction is considerably subject to the influence of the temperature of the sensor cell. Therefore, considering the extremely low concentration of the SOx included in the exhaust gas, it is preferred that the temperature of the sensor cell is maintained at a constant temperature. Thus, in the aforementioned embodiment, the heater may be controlled so as to maintain the temperature of the sensor cell at a constant temperature. According to this, the SOx concentration is detected more accurately.

<Sensor Mounting Position>

Further, in case that a catalyst for purifying components included in the exhaust gas is provided on the exhaust pipe, the SOx included in the exhaust gas may be trapped by the catalyst. In this case, if the limiting current type sensor is mounted on the exhaust pipe downstream of the catalyst, the SOx concentration may not be detected accurately. Thus, in the aforementioned embodiment, in case that the catalyst is provided on the exhaust pipe, it is preferred that the limiting current type sensor is mounted on the exhaust pipe upstream of the catalyst.

<Second Embodiment>

The second embodiment will be described. It should be noted that the configuration and the control according to the second embodiment which will not be described below are the same as those according to the first embodiment or are those derived obviously from those according to the first embodiment in consideration of those according to the second embodiment which will be described below.

<SOx Concentration Detection/Sulfur Poisoning Regeneration According to the Second Embodiment>

According to the second embodiment, the applied voltage is constantly maintained at 0.4V. Then, in the SOx concentration detection according to the second embodiment, the applied voltage is raised from 0.4V to 0.8V and then, the applied voltage is lowered from 0.8V to 0.4V. At this time, the ECU judges if the absolute value of the peak value of the output current input to the ECU while the applied voltage is lowered from 0.8V to 0.4V is larger than or equal to a first predetermined value. In this regard, in case that the absolute value of the peak value is larger than or equal to the first predetermined value, the ECU performs a sulfur poisoning regeneration control (the detail of this control will be described later). On the other hand, in case that the absolute value of the peak value is smaller than the first predetermined value, the ECU calculates (that is, detects) the SOx concentration by using the peak value and the reference current.

<Predetermined Value According to the Second Embodiment>

It should be noted that the first predetermined value according to the second embodiment is, for example, set as follows. The sulfur component of the SOx included in the exhaust gas may adhere to the first sensor electrode. From the study of the inventors of this application, it has been realized that this adhering sulfur amount (that is, an amount of the sulfur adhering to the first sensor electrode) increases, the absolute value of the peak value increases. Then, in case that this adhering sulfur amount is considerably large, the detection accuracy by the limiting current type sensor (in particular, the detection accuracy of the SOx concentration) may be decreased. Therefore, in case that the adhering sulfur amount is large, it is preferred to remove the sulfur adhering to the first sensor electrode (that is, perform the sulfur poisoning regeneration control). Thus, for example, the absolute value of the peak value (that is, the absolute value of the peak value of the output current input to the ECU while the applied voltage is lowered from 0.8V to 0.4V) in which the sulfur poisoning regeneration control should be performed is set as the first predetermined value according to the second embodiment.

<Sulfur Poisoning Regeneration Control>

It should be noted that a known control, for example, a control for raising the applied voltage to a relatively high voltage (for example, a voltage higher than or equal to 0.8V and in particular, a voltage equal to 1.0V) can be employed as the sulfur poisoning regeneration control.

<Advantage of the SOx Concentration Detection Device According to the Second Embodiment>

According to the SOx concentration detection device according to the second embodiment, in case that the detection accuracy of the sensor may be decreased due to the sulfur poisoning (that is, the adhering of the sulfur to the first sensor electrode), the sulfur poisoning regeneration control is performed. In other words, as far as there is no possibility that the decrease of the detection accuracy of the sensor due to the sulfur poisoning occurs, the detection of the SOx concentration is performed. Thus, according to the SOx concentration detection device according to the second embodiment, the SOx concentration can be detected more accurately.

<SOx Concentration Detection Flow According to the Second Embodiment>

An example of the SOx concentration detection flow according to the second embodiment will be described. This flow is shown in FIG. 12.

Figure 12:
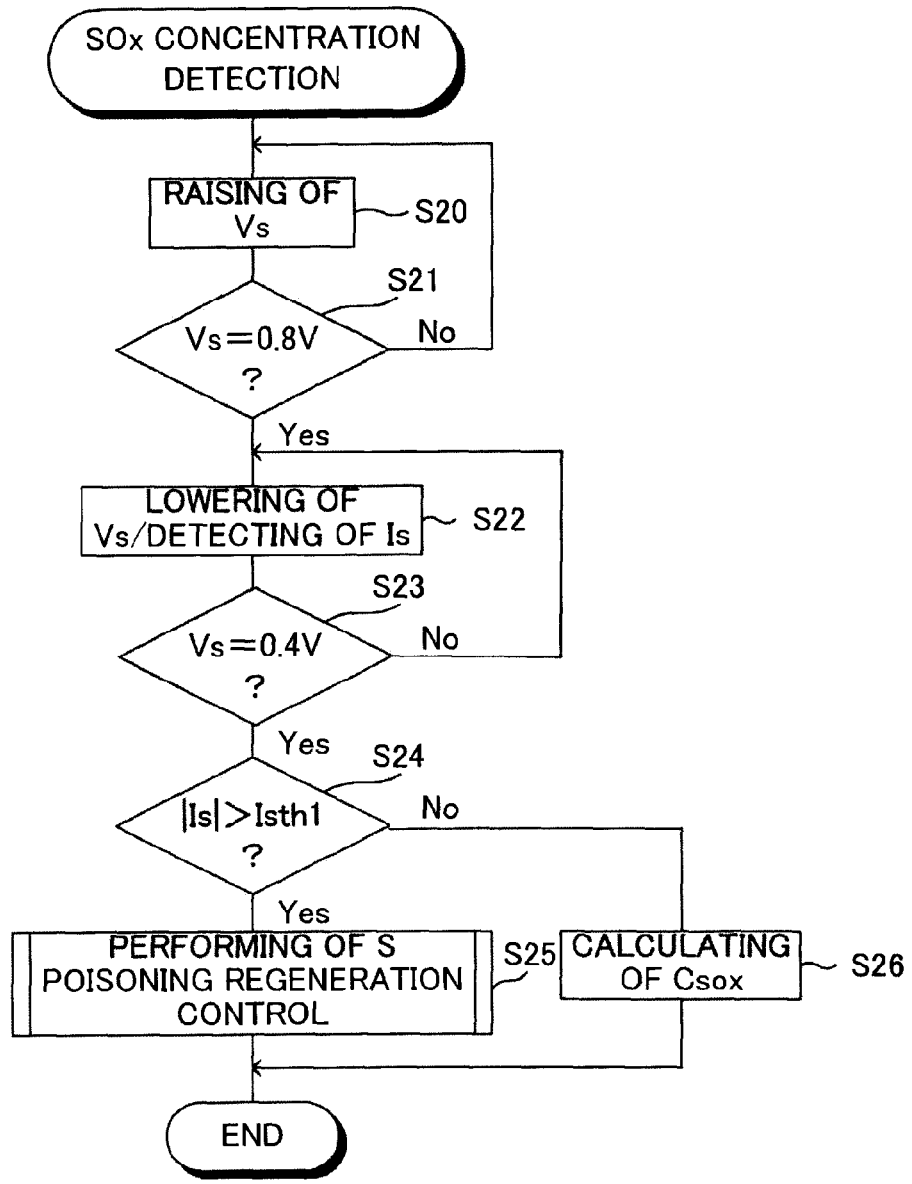
FIG. 12 shows an example of a SOx concentration detection flow according to the second embodiment.

When the flow shown in FIG. 12 starts, the applied voltage is maintained at 0.4V. Then, at the step 20, the applied voltage Vs is raised from 0.4V toward 0.8V. Next, at the step 21, it is judged if the applied voltage Vs reaches 0.8V (Vs=0.8V). In this regard, when it is judged that Vs=0.8V, the flow proceeds to the step 22. On the other hand, when it is not judged that Vs=0.8V, the flow returns to the step 20. Therefore, until it is judged that Vs=0.8V at the step 21, the raising of the applied voltage Vs is continued.

At the step 22, the applied voltage Vs is lowered from 0.8V toward 0.4V and the output current Is is detected. Next, at the step 23, it is judged if the applied voltage Vs reaches 0.4V (Vs=0.4V). In this regard, when it is judged that Vs=0.4V, the flow proceeds to the step 24. On the other hand, when it is not judged that Vs=0.4V, the flow returns to the step 22. Therefore, until it is judged that Vs=0.4V at the step 23, the lowering of the applied voltage Vs and the detecting of the output current Is are continued.

At the step 24, it is judged if the absolute value |Is| of the peak value of the output current Is detected at the step 22 is larger than a first predetermined value Isth1 (|Is|>Isth1). In this regard, when it is judged that |Is|>Isth1, the flow proceeds to the step 25 where the sulfur poisoning regeneration control is performed and then, the flow ends. On the other hand, when it is not judged that |Is|>Isth1, the flow proceeds to the step 26 where the SOx concentration Csox is calculated on the basis of the peak value of the output current Is detected at the step 22 and then, the flow ends.

<Third Embodiment>

The third embodiment will be described. It should be noted that the configuration and the control according to the third embodiment which will not be described below are the same as those according to the aforementioned embodiments or are those derived obviously from those according to the aforementioned embodiments in consideration of those according to the third embodiment which will be described below.

<SOx Concentration Detection/Fuel Property Malfunction Alert According to the Third Embodiment>

According to the third embodiment, the applied voltage is constantly maintained at 0.4V. Then, in the SOx concentration detection according to the third embodiment, the applied voltage is raised from 0.4V to 0.8V and then, the applied voltage is lowered from 0.8V to 0.4V. At this time, the ECU judges if the absolute value of the peak value of the output current input to the ECU while the applied voltage is lowered from 0.8V to 0.4V is larger than or equal to a second predetermined value. In this regard, in case that the absolute value of the peak value is larger than or equal to the second predetermined value, the ECU alerts the malfunction of the property of the fuel. On the other hand, in case that the absolute value of the peak value is smaller than the second predetermined value, the ECU calculates (that is, detects) the SOx concentration by using the peak value and the reference current.

<Predetermined Value According to the Third Embodiment>

It should be noted that the second predetermined value according to the third embodiment is, for example, set as follows. As described above, the sulfur component of the SOx included in the exhaust gas may adhere to the first sensor electrode and from the study of the inventors of this application, it has been realized that the adhering sulfur amount increases, the absolute value of the peak value increases. Then, in case that this adhering sulfur amount is considerably large, the detection accuracy by the limiting current type sensor (in particular, the detection accuracy of the SOx concentration) may be decreased. In this regard, the high concentration of the SOx included in the exhaust gas is one of the reason for the increase of the adhering sulfur amount. Then, as the concentration of the sulfur component included in the fuel increases, the concentration of the SOx included in the exhaust gas increases. Therefore, in case that the concentration of the sulfur component included in the fuel is unacceptably high and therefore, the malfunction of the property of the fuel may occur, it is preferred to alert the malfunction.

Thus, for example, a value appropriately selected from values larger than or equal to a minimum value of the absolute value of the peak value (that is, the absolute value of the peak value of the output current input to the ECU while the applied voltage is lowered from 0.8V to 0.4V) in case that the property of the fuel is not within an acceptable property range (in particular, in case that the concentration of the sulfur included in the fuel is higher than an acceptable concentration) is set as the second predetermined value according to the third embodiment.

It should be noted that the second predetermined value according to the third embodiment may be the same or different from the first predetermined value according to the second embodiment.

<Advantage of the SOx Concentration Detection Device According to the Third Embodiment>

According to the SOx concentration detection device according to the third embodiment, in case that the malfunction of the property of the fuel may occur, the malfunction is alerted and therefore, a user of the SOx concentration detection device can realize that the malfunction of the property of the fuel may occur.

<SOx Concentration Detection Flow According to the Third Embodiment>

An example of the SOx concentration detection flow according to the third embodiment will be described. This flow is shown in FIG. 13.

Figure 13:
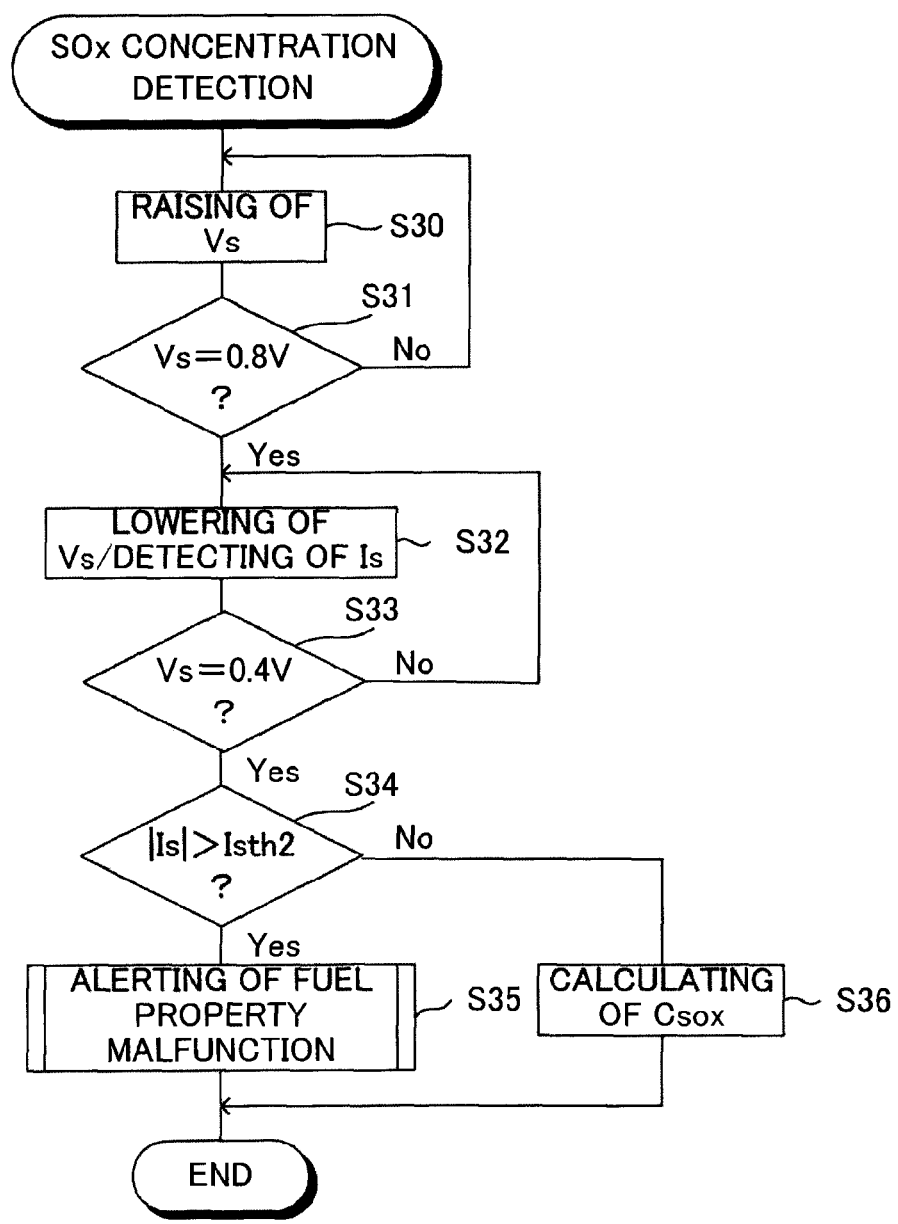
FIG. 13 shows an example of a SOx concentration detection flow according to the third embodiment.

When the flow shown in FIG. 13 starts, the applied voltage is maintained at 0.4V. Then, at the step 30, the applied voltage Vs is raised from 0.4V toward 0.8V. Next, at the step 31, it is judged if the applied voltage Vs reaches 0.8V (Vs=0.8V). In this regard, when it is judged that Vs=0.8V, the flow proceeds to the step 32. On the other hand, when it is not judged that Vs=0.8V, the flow returns to the step 30. Therefore, until it is judged that Vs=0.8V at the step 31, the raising of the applied voltage Vs is continued.

At the step 32, the applied voltage Vs is lowered from 0.8V toward 0.4V and the output current Is is detected. Next, at the step 33, it is judged if the applied voltage Vs reaches 0.4V (Vs=0.4V). In this regard, when it is judged that Vs=0.4V, the flow proceeds to the step 34. On the other hand, when it is not judged that Vs=0.4V, the flow returns to the step 32. Therefore, until it is judged that Vs=0.4V at the step 33, the lowering of the applied voltage Vs and the detecting of the output current Is are continued.

At the step 34, it is judged if the absolute value |Is| of the peak value of the output current Is detected at the step 32 is larger than a second predetermined value Isth2 (|Is|>Isth2). In this regard, when it is judged that |Is|>Isth2, the flow proceeds to the step 35 where the malfunction of the property of the fuel is alerted and then, the flow ends. On the other hand, when it is not judged that |Is|>Isth2, the flow proceeds to the step 36 where the SOx concentration Csox is calculated on the basis of the peak value of the output current Is detected at the step 32 and then, the flow ends.

<Fourth Embodiment>

The fourth embodiment will be described. It should be noted that the configuration and the control according to the fourth embodiment which will not be described below are the same as those according to the aforementioned embodiments or are those derived obviously from those according to the aforementioned embodiments in consideration of those according to the fourth embodiment which will be described below.

<SOx Concentration Detection/Air-Fuel Ratio Detection According to the Fourth Embodiment>

According to the fourth embodiment, the applied voltage is constantly maintained at 0.4V. That is, a voltage of 0.4V is constantly applied to the sensor cell. In this regard, the voltage of 0.4V is higher than or equal to the voltage Vth shown in FIG. 2 and is a voltage in which the sensor cell output current is constant independently of the sensor cell applied voltage in case that the air-fuel ratio of the exhaust gas is constant.

Then, in the SOx concentration/air-fuel ratio detection according to the fourth embodiment, the ECU calculates (that is, detects) the air-fuel ratio from the relationship shown in FIG. 2 on the basis of the sensor cell output current when the voltage of 0.4V is constantly applied to the sensor cell.

On the other hand, in case that the detection of the SOx concentration is required, the sensor cell applied voltage is raised from 0.4V to 0.8V and then, the sensor cell applied voltage is lowered from 0.8V to 0.4V. At this time, the ECU calculates (detects) the SOx concentration by using the peak value of the output current input to the ECU and the reference current while the sensor cell applied voltage is lowered from 0.8V to 0.4V.

Further, after the sensor cell applied voltage is lowered from 0.8V to 0.4V, the ECU calculates (that is, detects) the air-fuel ratio from the relationship shown in FIG. 2 on the basis of the sensor cell output current. Of course, at this time, the sensor cell applied voltage is maintained at 0.4V.

It should be noted that in case that the 2 cell type limiting current type sensor is used for the SOx concentration/air-fuel ratio detection according to the fourth embodiment, when the detection of the air-fuel ratio is performed, the voltage applied to the pump cell 15 is made to be zero.

<Advantage of SOx Concentration Detection Device According to the Fourth Embodiment>

According to the fourth embodiment, the air-fuel ratio of the exhaust gas and the concentration of the SOx included in the exhaust gas can be detected by the single sensor.

<SOx Concentration/Air-Fuel Ratio Detection Flow According to the Fourth Embodiment>

An example of a SOx concentration/air-fuel ratio detection flow according to the fourth embodiment will be described. This flow is shown in FIG. 14.

Figure 14:
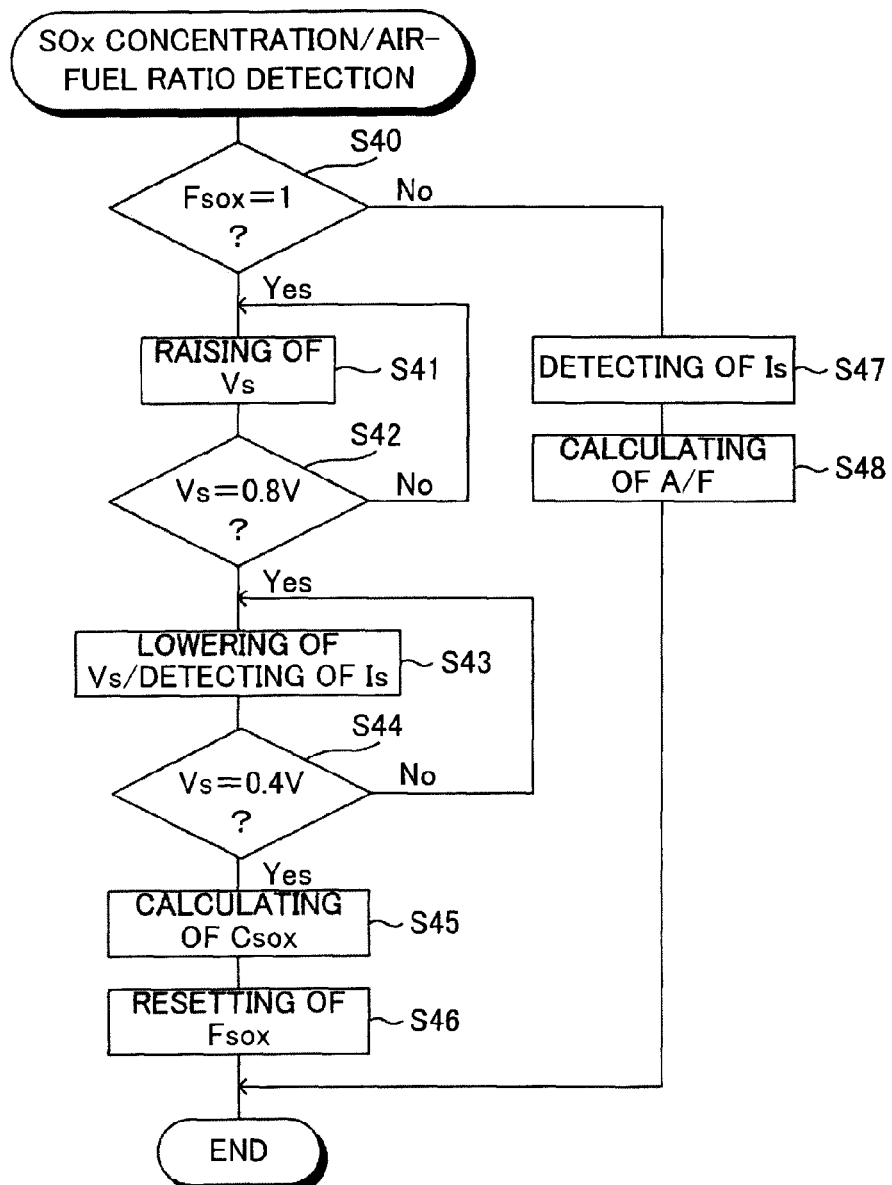
FIG. 14 shows an example of a SOx concentration/air-fuel ratio detection flow according to the fourth embodiment.

When the flow shown in FIG. 14 starts, the applied voltage is maintained at 0.4V. Then, at the step 40, it is judged if a SOx concentration detection flag Fsox is set (Fsox=1). This flag Fsox is set when the detection of the concentration of the SOx included in the exhaust gas is required and is reset when the detection of the concentration of the SOx included in the exhaust gas is completed. At the step 40, when it is judged that Fsox=1, the flow proceeds to the step 41. On the other hand, when it is not judged that Fsox=1, the flow proceeds to the step 47.

At the step 47, the output current Is is detected. Next, at the step 48, the air-fuel ratio A/F is calculated on the basis of the output current Is detected at the step 47 and then, the flow ends.

At the step 41, the applied voltage Vs is raised from 0.4V toward 0.8V. Next, at the step 42, it is judged if the applied voltage Vs reaches 0.8V (Vs=0.8V). In this regard, when it is judged that Vs=0.8V, the flow proceeds to the step 43. On the other hand, when it is not judged that Vs=0.8V, the flow returns to the step 41. Therefore, until it is judged that Vs=0.8V at the step 42, the raising of the applied voltage Vs is continued.

At the step 43, the applied voltage Vs is lowered from 0.8V toward 0.4V and the output current Is is detected. Next, at the step 44, it is judged if the applied voltage Vs reaches 0.4V (Vs=0.4V). In this regard, when it is judged that Vs=0.4V, the flow proceeds to the step 45. On the other hand, when it is not judged that Vs=0.4V, the flow returns to the step 43. Therefore, until it is judged that Vs=0.4V at the step 44, the lowering of the applied voltage Vs and the detecting of the output current Is are continued.

At the step 45, the SOx concentration Csox is calculated on the basis of the peak value of the output current Is detected at the step 43. Next, at the step 46, the SOx concentration detection flag Fsox is reset and then, the flow ends.

It should be noted that in the SOx concentration detection according to the aforementioned embodiments, the applied voltage is raised before the applied voltage is lowered. However, in case that the applied voltage is lowered, even if the applied voltage is not raised prior to the lowering of the applied voltage, the advantages of the aforementioned embodiments can be at least obtained.

Further, in the aforementioned embodiments, the concentration of the oxygen as well as the concentration of the SOx are detected by using the output current of the sensor. However, only the concentration of the SOx may be detected by using the output current of the sensor.

The invention claimed is:

1. A SOx concentration detection device of an internal combustion engine, comprising:
a limiting current type sensor; and a control unit that controls a voltage applied to the sensor and detecting a concentration of a SOx included in an exhaust gas discharged from the engine by using an output current of the sensor, wherein the control unit is configured to detect the concentration of the SOx included in the exhaust gas discharged from the engine by using the output current of the sensor while lowering the voltage applied to the sensor from a predetermined voltage, and wherein the control unit is configured to use, as the output current for the detection of the SOx concentration, a peak value of the output current of the sensor while lowering the voltage applied to the sensor from the predetermined voltage.

2. The SOx concentration detection device as set forth in claim 1, wherein the control unit is configured:

to apply a voltage lower than the predetermined voltage to the sensor after lowering the voltage applied to the sensor from the predetermined voltage; and to detect a concentration of an oxygen included in the exhaust gas by using the output current of the sensor when the voltage lower than the predetermined voltage is applied to the sensor.

3. The SOx concentration detection device as set forth in any of claim 1, wherein the control unit is configured to raise the voltage applied to the sensor from the voltage lower than the predetermined voltage to the predetermined voltage before lowering the voltage applied to the sensor from the predetermined voltage.

4. The SOx concentration detection device as set forth in claim 3, wherein the control unit is configured:

to apply the voltage lower than the predetermined voltage to the sensor before raising the voltage applied to the sensor to the predetermined voltage; and to detect a concentration of an oxygen included in the exhaust gas by using the output current of the sensor when applying the voltage lower than the predetermined voltage to the sensor.

5. The SOx concentration detection device as set forth in claim 1, wherein the predetermined voltage is a voltage higher than or equal to 0.8V.

6. The SOx concentration detection device as set forth in claim 1, wherein the voltage applied to the sensor when the lowering of the voltage applied to the sensor from the predetermined voltage is ended is a voltage lower than or equal to 0.7V.

7. The SOx concentration detection device as set forth in claim 1, wherein the control unit is configured to lower the voltage applied to the sensor from the predetermined voltage at a speed smaller than or equal to a speed of a change of a voltage having 100 Hz.

8. The SOx concentration detection device as set forth in claim 3, wherein the control unit is configured:

to raise the voltage applied to the sensor from the voltage lower than the predetermined voltage at a speed smaller than or equal to a speed of a change of a voltage having 100 Hz; and to lower the voltage applied to the sensor from the predetermined voltage at a speed smaller than or equal to a speed of a change of a voltage having 100 Hz.

9. The SOx concentration detection device as set forth claim 1, wherein the engine is a gasoline engine.

10. The SOx concentration detection device as set forth in claim 1, wherein the control unit is configured to perform a sulfur poisoning regeneration control for regenerating the sulfur poisoning of the sensor in case that an absolute value of the output current of the sensor while lowering the voltage applied to the sensor from the predetermined voltage is larger than or equal to a first predetermined value.

11. The SOx concentration detection device as set forth in claim 1, wherein the control unit is configured to alert a malfunction of a property of a fuel supplied to a combustion chamber of the engine in case that an absolute value of the output current of the sensor while lowering the voltage applied to the sensor from the predetermined voltage is larger than or equal to a second predetermined value.

12. A method for detecting a concentration of a SOx included in an exhaust gas discharged from an internal combustion engine having a limiting current type sensor, comprising:

lowering a voltage applied to the sensor from a predetermined voltage;

acquiring an output current of the sensor during the voltage lowering step; and detecting the concentration of the SOx included in the exhaust gas by using the output current acquired by the output current acquiring step, wherein a control unit is configured to use, as the output current for the detection of the SOx concentration, a peak value of the output current of the sensor while lowering the voltage applied to the sensor from the predetermined voltage.

13. The method as set forth in claim 12, wherein the method further comprises:

applying a voltage lower than the predetermined voltage to the sensor after the voltage lowering step; and detecting a concentration of an oxygen included in the exhaust gas by using the output current of the sensor during the post-lowing voltage applying step.

14. The method as set forth in claim 12, wherein the method further comprises:

applying a voltage lower than the predetermined voltage to the sensor before the voltage lowering step;

raising the voltage applied to the sensor to the predetermined voltage after the pre-lowering voltage applying step and before the voltage lowering step; and detecting a concentration of an oxygen included in the exhaust gas by using the output current of the sensor during the pre-lowering voltage applying step.

15. A limiting current type sensor used for detecting a concentration of a SOx included in an exhaust gas discharged from an internal combustion engine by using an output current of the sensor while a voltage applied to the sensor is lowered from a predetermined voltage, wherein a control unit is configured to use, as the output current for the detection of the SOx concentration, a peak value of the output current of the sensor while lowering the voltage applied to the sensor from the predetermined voltage.

16. The sensor as set forth in claim 15, wherein the sensor is used for detecting a concentration of an oxygen included in the exhaust gas by using the output current of the sensor when a voltage lower than the predetermined voltage is applied to the sensor after the voltage applied to the sensor is lowered from the predetermined voltage.

17. The sensor as set forth in claim 15, wherein the sensor is used for detecting a concentration of an oxygen included in the exhaust gas by using the output current of the sensor when a voltage lower than the predetermined voltage is applied to the sensor before the predetermined voltage is applied to the sensor.

* * * * *